US009474499B2

(12) United States Patent
Exelmans et al.

(10) Patent No.: US 9,474,499 B2
(45) Date of Patent: Oct. 25, 2016

(54) METHOD FOR THE DETERMINATION AND USE OF A STANDARD OPERATIONAL VALUE FOR THE DELAY TIME OF A RADIOGRAPHIC SYSTEM

(71) Applicant: Agfa HealthCare NV, Mortsel (BE)

(72) Inventors: Walter Exelmans, Mortsel (BE); Patrick Pandelaers, Mortsel (BE); Patrick Lambrechts, Mortsel (BE)

(73) Assignee: AGFA HEALTHCARE NV, Mortsel (BE)

( * ) Notice: Subject to any disclaimer, the term of this patent is extended or adjusted under 35 U.S.C. 154(b) by 211 days.

(21) Appl. No.: 14/394,757

(22) PCT Filed: Apr. 22, 2013

(86) PCT No.: PCT/EP2013/058272
§ 371 (c)(1),
(2) Date: Oct. 16, 2014

(87) PCT Pub. No.: WO2013/160235
PCT Pub. Date: Oct. 31, 2013

(65) Prior Publication Data
US 2015/0085987 A1  Mar. 26, 2015

(30) Foreign Application Priority Data
Apr. 23, 2012 (BE) .................................. 201200268

(51) Int. Cl.
*A61B 6/00* (2006.01)
(52) U.S. Cl.
CPC .................. *A61B 6/545* (2013.01); *A61B 6/40* (2013.01); *A61B 6/467* (2013.01); *A61B 6/542* (2013.01)

(58) Field of Classification Search
CPC ........ A61B 6/40; A61B 6/467; A61B 6/542; A61B 6/545
See application file for complete search history.

(56) References Cited

U.S. PATENT DOCUMENTS

| 2009/0129546 | A1 | 5/2009 | Newman et al. |
| 2011/0123001 | A1 | 5/2011 | Kopcienski et al. |
| 2012/0134474 | A1* | 5/2012 | Duca .................... A61B 6/4233 378/96 |
| 2013/0003933 | A1* | 1/2013 | Peterson .................. A61B 6/40 378/91 |

FOREIGN PATENT DOCUMENTS

EP         2 209 422 A1    7/2010

OTHER PUBLICATIONS

Official Communication issued in International Patent Application No. PCT/EP2013/058272, mailed on May 29, 2013.
Rowlands et al., "Flat Panel Detectors for Digital Radiography," Handbook of Medical Imaging, vol. 1, Chapter 4, SPIE, 2000, pp. 223-328.

* cited by examiner

*Primary Examiner* — David J Makiya
*Assistant Examiner* — Dani Fox
(74) *Attorney, Agent, or Firm* — Keating and Bennett, LLP

(57) ABSTRACT

A method for the determination of the delay time of a radiographic generator and to the setting of a standard value for such delay time. According to the method it is determined by a series of decreasing chosen values for the delay time whether a signal for the confirmation of the start of the radiographic exposure is rendered by the radiographic generator. The last value of the chosen delay time whereby still such a confirmation signal is rendered, is retained as standard operational value for the delay time of the radiographic system.

7 Claims, 2 Drawing Sheets

METHOD FOR THE DETERMINATION AND USE OF A STANDARD OPERATIONAL VALUE FOR THE DELAY TIME OF A RADIOGRAPHIC SYSTEM

CROSS-REFERENCE TO RELATED APPLICATIONS

This application is a 371 National Stage application of PCT/EP2013/058272, filed Apr. 22, 2013. This application claims the benefit of Belgian Application No. 201200268, filed Apr. 23, 2012, which is incorporated by reference herein in its entirety.

BACKGROUND OF THE INVENTION

1. Field of the Invention

The present invention relates to a method for the determination and use of a standard operational value for the delay time of a radiographic system used in medical radiographic applications. More in particular the method relates to a technique to determine the delay time or start-time of a generator, used in combination with a digital radiographic detector, a so-called FPD, Flat Panel Detector, and to use same as standard operational value for radiographic exposures.

2. Description of the Related Art

It is known that radiographic illumination has important applications in medical imaging, whereby the medical advantages for the patient largely exceed the small risk of damage resulting from such radiographic illumination. The formation of images is a result of the fact that radiographic illumination, depending on the energy, passes through most soft tissues, but does not pass the harder calcium-containing tissue. So, as an example, bones will bar most radiographic illumination whereas cartilage will bar such illumination to a much lesser extent. As a result, since more than a century, the human skeleton can easily be visualised by radiographic illumination. Radiographic illumination is also applied in medicine in radio therapeutic applications. For the application of the present invention however radiographic illumination is used for medical imaging applications, more in particular for medical diagnosis.

Radiographic illumination generally is generated in an X-ray tube as 'Bremsstrahlung'. An example of such an x-ray tube is shown in FIG. 2.

This radiation is generated when accelerated electrons impinge on a target, mostly made of tungsten of another hard material such as molybdenum with a melting point above 2 000 degrees Celsius. The electrons are accelerated under vacuum (10-5 Pascal) by use of an electric current. A tension difference (anode tension) generates such field between the cathode K and the anode A. Electrons are liberated from the Cathode K by heating same, for example by a resistance wire of filament, whereupon an incandescent tension is applied, causing an incandescent current that generates a local heating.

At around 2 700 K electrons are generated around the tungsten filament that can escape from such material at these elevated temperatures. As such electrons are negatively charged, they are accelerated by a strong electric field (30-150 kV depending on the application) over a distance of a few millimetre from the negative cathode to the positive anode. The maximal energy of the radiographic illumination generated in this way is proportional to the electrical voltage applied; therefore is usually is expressed as kilo-electron volt. The intensity is depending on the electrical current that is generated. This is expressed in mA (mill amperes).

When generating such intense radiographic illumination, the target, the anode, is heated intensively. As a result, radiographic tubes are provided with cooling arrangements (for example water cooling and/or are characterised by a high rotational speed of the target (rotating-anode).

The anode mostly is made of metal. In the anode material the electrons are intensively slowed down, producing a radiographic illumination having an energy comprised between O and the total voltage of the electric field. This illumination is called Bremsstrahlung. On top hereof a high number of such electrons will be slowed down by collision with electrons in the anode material and will ionise atoms by liberating electrons from the inner shells. When such electrons fall back to such inner shells, so-called characteristic radiation is generated, depending on the kind of metal the anode is made of. In case of a copper-anode this radiation is around 8 keV, whereas in case of molybdenum this radiation amounts to approx. 18 keV. The total charge of a radiation tube is a few kilowatts, the surface whereupon the electrons impinge is between 0.5 and 10 square millimetre.

For use in medical imaging applications, two kinds of radiation tubes are used, differing as regards the construction of the anode. All tubes consist of a glass tube wherein the all components are present under high vacuum. One type of radiation tube comprises a fixed anode, whereas the other comprises a rotating anode. Because all tubes and casings are fully closed, it is not possible to use a cooling medium from outside, as was the case in the past. The only possibility is the discharging of the energy generated by radiation. To this end, the tube is surrounded by an amount of air-free high-quality oil. A switch is foreseen that will automatically interrupt the current in case of expansion of the oil by heating; in this way the tube is protected against overheating.

This is the original model, whereby the anode usually is made of copper, characterised by an excellent heat conductivity.

This model is mostly used in apparatuses with a limited power as used for example in dentist applications, in portable and mobile units.

To achieve an improved discharge of the heat, the rotating anode concept has been developed. In this concept, use is made of a massive disc of tungsten or an alloy of tungsten and rhenium. The place where the electrons impinge is not limited to approximately 1 square centimetre, but consists of a circle over the disc surface, the so-called line focus. Also a second incandescent filament can be mounted in the cathode, that focuses on a smaller of larger surface on the anode. A small target surface (focus) is characterised by less scattering and thus less geometrical unsharpness. For small objects (hands, feet, small joints) one usually chooses the smallest possible focus for a maximal rendering of details.

The anode is formed by the disc, the support and the anode body that functions as the rotor of an electromotor. At the outside magnets are mounted (stator) that enable the anode to quickly turn around. Depending on the tube-type the rotating velocity is situated between 4000 and 9000 revolutions per minute. The angle of the anode is usually situated between 10° and 20°, which is much smaller than in case a fixed anode is used. Tubes having a rotating anode usually have much more components that fixed-anode tubes and the steering thereof requires much more electronic circuitry. Consequently these models are much more expensive compared to the more simple models. The efficiency of tubes with a rotating anode is however much higher and the application of this type of tubes practically has no limits.

Preferred embodiments of the present invention as described hereinafter relate to radiation tubes with a rotating anode; these types of tubes are most common nowadays, in particular for general purpose radiography (genrad), as well as for mammographic applications (mammo).

As is known to those skilled in the art, in case of a radiographic illumination with a DR Panel, the generator should first receive a signal that the anode should be brought to speed, and the filament or incandescent wire of the cathode should be heated to a red/white state.

After a certain amount of time which is required for the above—this is the so-called generator delay time or start-up time—the expose or illumination button can be activated, whereby the generator is brought under high tension.

In case the operator activates both buttons simultaneously, or in case of a combined prep-expose button, activates the button at full, a pre-determined fixed delay time will cause the high tension to occur only after the anode is brought to speed and the filament or incandescent wire is heated to the red/white state.

This start-up or delay time of the radiographic generator should be known.

These times differ for the various types of radiographic generators that are on the market.

This problem in particular arises when an existing radiographic exposure unit in a hospital was used in combination with radiographic detectors such as film or stimulable phosphors, and now should be used in combination with fully digital radiographic detectors, such as flat panel detectors.

This is the so-called retrofit situation, known to the person skilled in the art of medical radiography.

One of the crucial differences between the use of radiographic films or stimulable phosphors, as contrary to fully digitized panels, is that films and stimulable phosphors are always 'ready' to be exposed.

The only limitation for a film is that it should not be exposed and/or developed in an earlier stage, and in case of a stimulable phosphor screen, that it has been erased after a prior exposure.

Provided these conditions are met, both radiographic media are always apt to be used in a radiographic exposure.

The radiographic workflow in case a fully digitized radiographic panel is used, on the contrary, is rather different. The reason for this is that in most cases a radiographic digital panel should first be reset. This resetting is known to the person skilled in the art, and is described amongst others in the Handbook of Medical Imaging, Vol. 1, Chapter 4: Flat Panel Imagers for digital radiography, (ed. R. V. Matter et al., SPIE Press, Bellingham, 2000.)

The resetting of a radiographic digital panel, and the problems caused hereby in case of a change-over of an existing radiographic exposure unit, previously used in combination with film or stimulable phosphor plates, to a unit based on the use of digital radiographic detectors, is published in a great number of earlier patent specifications, amongst others in EP 2 209 422.

The global aim in case of a radiographic exposure is that the integration time of the panel or the digital radiographic detector overlaps with the exposure-time of the generator. More in particular, the integration time should somewhat exceed the exposure time to be sure no radiographic diagnostic information is lost.

To this end it is essential to know the applicable generator delay time.

Indeed, suppose the start-up of the generator would coincide with the integration time of the direct radiographic panel, then it is not excluded that the integration time has expired at the moment the effective exposure starts. Such a procedure evidently would not lead to an image useful for medical diagnosis.

In practice, a radiographic exposure can take place according to two different ways. First the radiographic operator activates the prep button of the apparatus, e.g. on the retrofit box.

The patient to be radiographed is then requested to keep still and not to breathe temporarily (in case of a chest exposure). As set forth supra, the generator then receives a signal to bring the anode to speed and to heat the filament.

In case the operator waits sufficiently long for the activation of the expose button, until the generator's rotating anode is effectively up to speed (the so-called generator delay time), no problem arises.

When the exposure button is activated by the operator, a signal is sent to the DR panel to reset same, and once this is done, over the retrofit box a signal is sent to the generator to start the exposure.

The generator is ready to perform same because its generator delay time has expired, in other words, because the generator has had enough time to prepare the exposure.

The problem arises when—as is often the case in practical circumstances—the operator activates, e.g. by pressing, the prep and exposure buttons simultaneously, or in case the operator pushes through (in case the prep and exposure buttons are integrated in one and the same button or device, that can be activated as well in part as in full). In such a case, the problem can arise that the generator receives an expose signal at a time the generator is not ready for this, in other words, because its anode is not yet brought to speed, and/or the filament wire is not sufficiently heated.

In such a preferred embodiment, the generator will necessarily wait to commence the exposure until the time the rotating anode is up to speed, but in the meantime the panel is ready to receive the radiographic illumination, differently phrased, the panel is integrating same, but there does not exist a meaningful radiographic signal to integrate. In the worst case scenario, the generator starts to perform exposure at a time the panel again is closed, because for example its integration time has expired.

In such scenario the above situation often leads to a so-called retake, which means that the patient will be exposed again. This evidently should be avoided, given the inherent harmful effect of any radiographic exposure on the health condition of patients.

SUMMARY OF THE INVENTION

The present invention overcomes the abovementioned problems and disadvantages.

Preferred embodiments of the present invention relate to a method for the determination of the delay time of a radiographic generator used in medical radiographic systems, and the use hereof as standard operational value for the delay time of the corresponding radiographic system, comprising the following steps:

selection of a sufficiently high delay-time for the radiographic generator on a retrofit box;

Simultaneous transmission of the preparation- and exposure signal from the retrofit box to the generator console;

Determining whether at the expiration of the selected delay time a confirmation signal for the start of the radiographic exposure has been submitted by the radiographic generator;

In case such a confirmation signal has been submitted, repeating the abovementioned three steps, whereby the delay-time is reduced by a factor two;

In case no such confirmation signal has been submitted, repeating once the abovementioned three steps, whereby a value is selected for the delay time mid-way the value whereby a confirmation signal still has been obtained, and the value whereby such signal has not been obtained any more;

The last value of the selected delay-time whereby a confirmation signal still has been given by the radiographic generator, is retained as standard operational value for the delay time of the radiographic system by the retrofit box.

According to a preferred embodiment of the invention, the method comprises a step whereby the initially selected sufficiently high delay time amounts to at least 10 seconds.

According to a further preferred embodiment the method comprises a step whereby the preparation and exposure signals are submitted simultaneously by simultaneous activation of the preparation and exposure buttons on a retrofit box.

Preferred embodiments of the present invention also relate to a method for taking a radiographic exposure, whereby the radiographic image is captured by a radiographic digital detector and, in case the radiographic operator generates an exposure signal to the retrofit box at a time that the delay time of the generator, counted as from the submission of the preparation signal by the operator, has not expired yet, that the retrofit box transmits this exposure signal to the radiographic generator after expiration of the standard operational delay time as determined by the method as described above, and more in particular as described below, and counted as from the transmission of the preparation signal from the retrofit box to the radiographic generator.

According to a preferred embodiment of the above method, the retrofit box will transmit the exposure signal to the radiographic generator, after a positive reset signal has been received by the digital radiographic detector.

Preferred embodiments of the present invention also relate to a radiographic recording system, comprising a radiographic generator, a console and an exposure unit, a digital radiographic detector, a retrofit box including a detector that detects a preparation signal and an exposure signal, characterised in that the retrofit box uses a standard operational value for the delay time for the transmission of the exposure signal to the generator, whereby the standard operational value is determined by the method described as set forth above, and more in particular as set forth below.

According to a preferred embodiment of the the system, the detector of the preparation signal and the exposure signal comprises a two-stage push button operationally coupled to the retrofit box.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Figure 1:
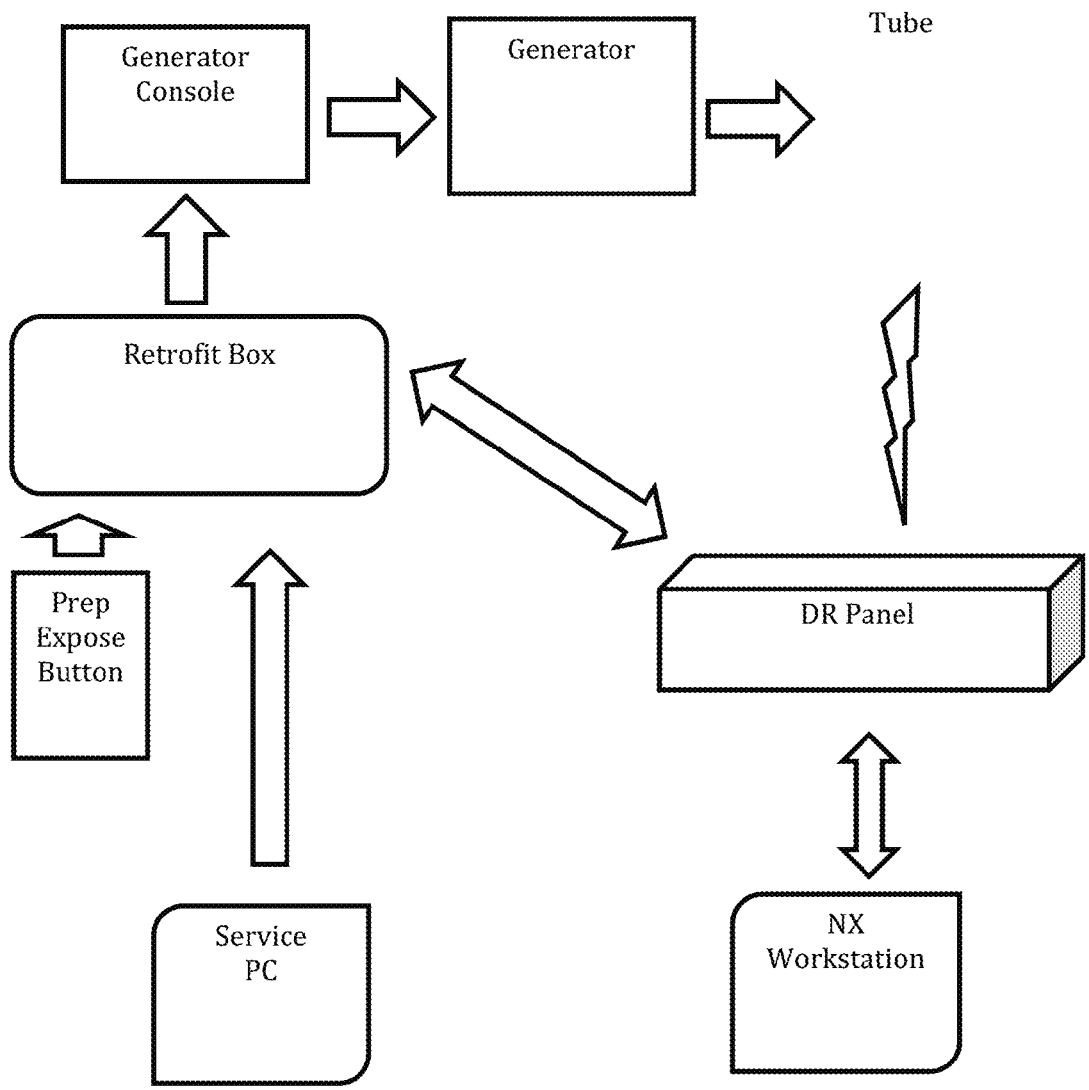
FIG. 1 shows a schematic bloc diagram of a radiographic configuration for the implementation of a method according to a preferred embodiment of the present invention.

According to the schematic block diagram of FIG. 1, the Generator Console shows a console from where the radiographic generator, shown by the bloc marked 'generator' can be steered. On its turn the generator takes care that the radiographic tube, marked by the bloc 'tube', emits radiographic emission, shown by the dashed arrow, that is captured by a radiographic digital detector. The digital radiographic detector is shown by the bloc marked 'DR Panel'.

This DR panel on its turn is connected to the workstation, shown by the bloc 'NX Workstation'. This workstation may comprise a display with related CPU, whereupon the radiographic image can be visualised for observation by a radiologist for determination of a clinical diagnosis.

The DR Panel is in operational communication with a central steering unit, called retrofit-box. The operation of such box is described hereinafter.

This unit also comprises a module that allows the operator to perform the necessary instructions to the radiographic unit, such instructions comprising a so-called prep and expose-signal.

These instructions can be transmitted to the retrofit box in a variety of manners.

A first preferred embodiment comprises a retrofit box having two separate push-buttons, one for the transmission of the prep signal, and a second one for the transmission of the expose signal. These commands may be integrated in one and the same push-button, that either can be pushed mid-way or at full for transmitting either the prep, or the expose command.

An alternative preferred embodiment is that these commands can be transmitted by a computing device, provided with either a keyboard or a touch screen.

The bloc denoted 'service PC' can also transmit such commands.

Figure 2:
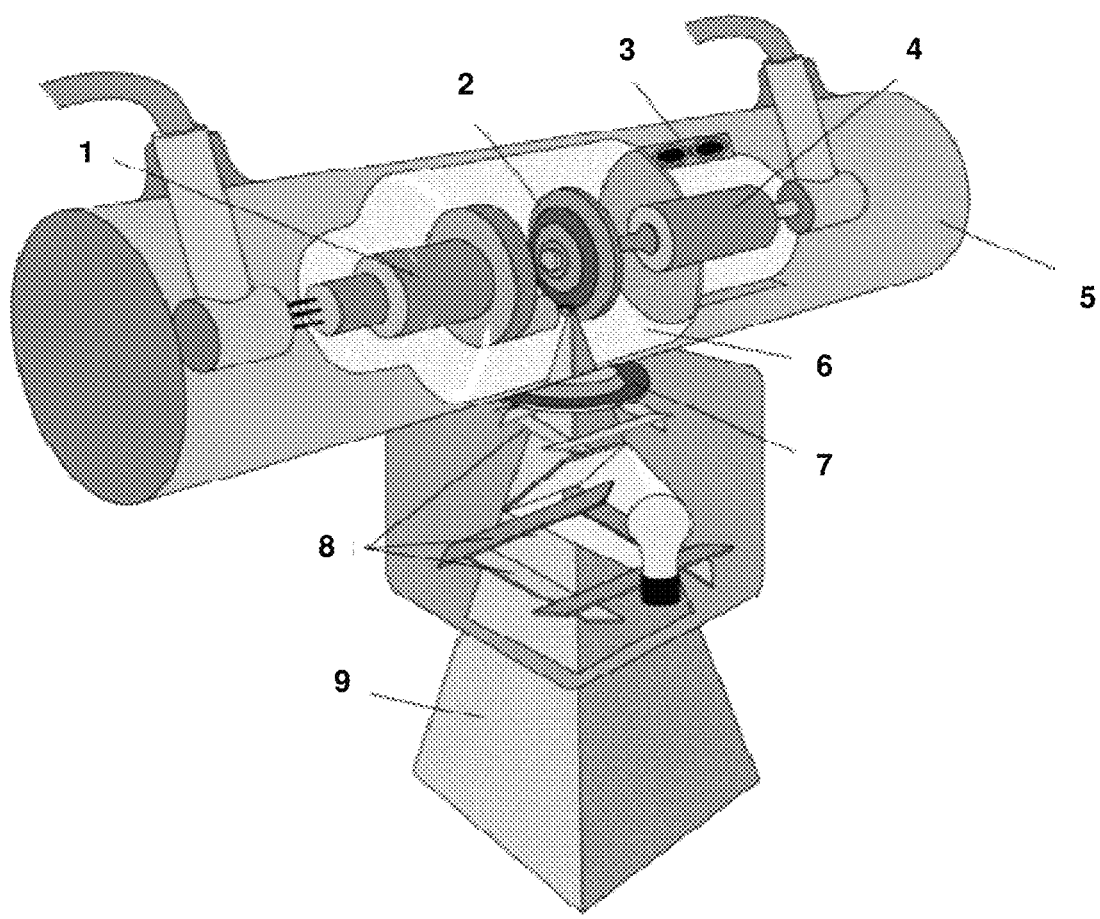
FIG. 2 shows a drawing in principle of a radiographic generator whereupon a preferred method of the present invention can be applied.

FIG. 2 shows a drawing in perspective of a radiographic generator, as it can be used in practice for radiographic exposures in a hospital. This generator comprises the following elements, that are shown in connection with the reference signs set forth below:

1: cathode;
2: rotating anode;
3: stator;
4: rotor;
5: tube of the radiographic illumination source;
6: glass casing;
7: filters;
8: collimators;
9: radiographic illumination bundle.

Definitions

Hereinafter are set forth—for a better understanding of the present invention—the definitions of a few terms used in the description that follows, as well as in some of the claims.

Also are mentioned the order of magnitude of some of the time periods or intervals that are mentioned in such definitions.

Integration time: this is the time during which the digital radiographic panel, or Flat Panel Detector, is 'open', this means integrates the signals. This time amounts to approximately 550 msec, so about half a second, up to 3 sec at maximum.

Exposure time: this is the time during which the radiographic generator effectively transmits radiographic illumination to the patient; this time in practice is more or less in the same order of magnitude as the integration time; this is a feature of the generator settings; this should be shorter than the integration time under practical circumstances, otherwise information is lost.

Prep-delay or generator delay-time: this is the time that runs from the receipt by the generator of a prep-signal, and the time that the rotating anode is up to speed, and/or the time that the filament wire or incandescent wire is up to temperature (red/white). This is dependant upon the type of generator and is in the order of magnitude of 0.5 up to 3 sec.

Panel delay time: a distinction should be made between the panel delay time and the generator delay time. The panel delay time is equal to the so-called reset time. This is the time that the radiographic detector needs before it can detect radiographic signals. This time is in the order of magnitude of 100 to 200 milliseconds. This still is something else than the panel wake-up time: this time amounts to approx. 2 seconds. Not all panels are characterised by a wake-up time. There exist Flat Panel Detectors that are always in wake-up state. The total panel delay time thus is the sum of the above two values, so amounts to approx. 2.1 up to 2.2 sec.

Radiographic digital detector: this is a radiographic detector for the direct digital detection of radiographic images on a storage medium. Examples of such detectors are described in the Handbook of Medical Imaging, previously cited.

An essential item is the determination of the prep delay time of the radiographic generator.

When the prep-button is activated, the prep-signal is submitted to the radiographic generator, implying that the rotating anode is brought up to speed, and the filament or incandescent wire is heated (this takes a delay time 1).

Also at the time of the submission of the prep signal, the DR panel is activated (if necessary). The patient waits and stops breathing for a while (in case of a chest exposure). After the expiration of this delay the exposure or effective illumination can start.

When the expose button is activated, a signal is sent from the retrofit box to the panel, to start the reset. When this has taken place, over the retrofit box a signal is sent to the generator to apply the high voltage or tension over the cathode/anode system. When this has effectively taken place (implying a delay 2), the actual exposure can start, and thus also the integration of the DR panel. When this stops, the DR panel is read-out.

All of the above preferably is implemented by hardware links although wireless communications between the different elements of a radiographic system can also be used.

The goal of preferred embodiments of the present invention now is to determine the delay 1, this is the time the generator needs to be up to speed, more in particular to bring the rotating anode to its usual operational speed, and to heat the filament wire to its usual operational temperature.

This is a stage that takes place before the actual radiographic exposure, a preparatory stage.

In practice, any radiographic generator yields a signal either visually or orally, to indicate that the actual radiographic exposure starts. This can take the form of a ding-dong, a light that starts to shine or blink, an icon on a display, or a combination of any of the above means.

The generator is put in a so-called 'free exposure state', this means without being coupled to a digital radiographic detector. To this end, use can be made of a film, or stimulable phosphor screen (Computed Radiography, CR), or simply no image storage medium.

Suppose that the prep delay time of the apparatus is set at exactly 10 seconds. This means that in the retrofit box a delay time is set of 10 seconds, differently phrased, after the expiration of 10 seconds as from the activation of the prep and expose button, the expose signal is triggered.

A signal is then sent from the retrofit box to the generator to start the exposure. But if the generator after ten seconds is not fully up to speed and/or the filament wire is insufficiently heated, no exposure takes place. This time can be set in various installments, starting from a sufficiently high value, and gradually descending.

For the purpose of preferred embodiments of the present invention, a sufficiently high delay time should be understood as being a time value whereby the radiographic generator has brought its rotating anode fully up to operational speed, and whereby the filament wire is sufficiently heated for use in practice. For the majority of radiographic generators 10 seconds is sufficient for the above purposes; if need be one can start by setting the first value at 15 seconds for the delay-time.

At a given set time, one will note that the signal of the exposure of the generator will be notified; this is then the prep-delay time or start-up time for the given radiographic generator.

This time is determined by a binary method. After three to four attempts at various pre-determined time delays, one knows the prep delay time of the specific radiographic generator that is at hand.

Thereafter the retrofit box can be placed in the usual operational mode. The delay time of the radiographic generator is then known to the retrofit box.

How will then the sequence take place for a radiographic exposure with a retrofit box, for which the prep delay time of the operationally linked generator is known, and which is placed in its usual operational mode?

We start from the working assumption that the radiographic operator has activated the prep and exposure buttons simultaneously.

In practice this is not always the case. In case the operator activates first the prep button, causing the retrofit box to transmit the preparation signal to the radiographic generator, and the operator waits sufficiently long before activating the exposure button, the problem as set forth supra, does not arise.

In such a case, the radiographic generator will be ready (this means its anode will be fully operational and the filament wire sufficiently heated, at the moment the operator activates the expose button, and whereby the retrofit box transmits the corresponding exposure signal to the radiographic generator).

When the operator then pushes through, the prep signal is directly transmitted to the generator. The generator is then brought to speed, and has sufficient time for this action.

After expiration of the prep delay time, the retrofit box sends an exposure request signal to the DR panel. This will trigger the reset operation, which takes approximately 100 milliseconds. Thereafter the DR panel is ready to capture the image.

Thereafter the integration starts automatically. This triggers the expose signal OK, and over the retrofit box a signal is sent to the generator that it can start the exposure. The radiographic generator then effectively starts the radiographic exposure, whereupon the DR panel will capture and integrate the radiographic image.

So, in short: according to a preferred method of our invention it is determined by a series of decreasing chosen values for the delay time whether a signal for the confirmation of the start of the radiographic exposure is rendered by the radiographic generator. The last value of the chosen delay time whereby still such a confirmation signal is rendered, is retained as standard operational value for the delay time of the radiographic system.

More complex methods can be envisaged to determine the prep delay time. Such methods can be based on the signal to noise image parameters, on a shifting of the integration time, but these are unnecessarily complicated. The above described methods are characterised by its simplicity, and consequently by its robustness in practical circumstances.

What follows hereinafter is a description of a practical preferred embodiment of a method of the invention, applied in a real-life situation.

EXAMPLE

In a concrete example a method for the determination of the prep delay time comprised the following steps.

This method was applied using the following apparatus:
The radiographic generator used was a GENIT 80 kW apparatus, supplied by Siemens AG, Germany;
The radiographic tube used was an apparatus 'X-ray Tube Housing Assembly SV 150/40/80 C-100 L', available from Dunlee;
The generator console used was a Touch Desk (104 10 669) available from Siemens AG, Germany.

The generator was set in the 'free exposure state', simply by not using any image storage medium in the example according to a preferred embodiment of the invention.

The retrofit box is connected to the radiographic generator.

For the setting of the exposure parameters of the generator, use is being made of a two-point exposure: the exposure setting (the level of the high voltage applied) was set at 70 kV, and the exposure dose was set at 5 mAs.

At each of the following steps, the prep/expose button on the retrofit box was activated at full, this means prep and expose button were activated simultaneously.

In an initial step, the generator delay time is set at 10 sec. This means that after exposure of 10 sec, as from the transmittal of the prep signal from the retrofit box to the generator, the expose signal is equally sent from the retrofit box to the generator.

In this case, the generator yielded immediately an oral confirmation signal (by a buzzer), indicating that the exposure could effectively start after this period of 10 sec had expired.

This means that the generator delay time is effectively inferior to the set time of 10 sec. In a subsequent step, the generator delay time was set at a lower value, in this concrete case, at half the original value, so at 5 sec.

Again the button on the retrofit box is fully pressed, so prep and exposure button are both activated. We noted that after expiration of this time period of 5 seconds, again as from the transmittal of the prep signal to the generator, the expose signal is transmitted to the generator, and promptly hereupon the oral confirmation signal is given by the generator.

So the actual exposure started after expiration of these 5 seconds, indicating that the generator delay time was effectively shorter that the set time of 5 seconds.

Hereupon, in a next step, the generator delay time was set again at half the previous value, so at 2.5 sec.

Also in this case, promptly after the expiration of this delay time of 2.5 sec, a positive confirmation signal was noted. The effective generator delay time consequently was shorter than 2.5 sec.

Hereupon in a next step, the generator delay time was set at 1 second. In this case we did not note a positive confirmation signal after expiration of this time period of 1 second.

This means that the effective generator delay time is superior to 1 second.

As a result, in a next step the generator delay time was set at 1.5 sec. In this case again, after expiration of this period of 1.5 seconds, a positive confirmation signal was noted.

The conclusion from the above series of events is that the effective generator delay time is situated between 1 and 1.5 seconds. As a result the delay time was set at 1.5 seconds, and this value was used as standard operational value for the delay time of the radiographic system in further use.

By applying the above manner and method, it is assured that after expiration of this standard operational value, the generator effectively is apt to start the radiographic exposure.

After determination of the generator delay time by applying the above method, this time period was set as standard operational value in a retrofit box, and an exposure was performed by a radiographic digital detector marketed under the brand name PaxScan 4343 R, available from Varian Medical Systems, Salt Lake City, Utah, USA.

The problems cited at the introduction of this specification did not occur.

The radiographic imaging method when using such a digital flat panel detector in a usual operational mode is then as follows.

The prep/expose button on the retrofit box is fully pressed, whereupon a prep signal is transmitted to the generator. The generator will then bring the rotating anode at full operational speed, and takes care that the filament wire is fully heated. After expiration of the standard operational generator delay time of 1.5 seconds, a signal is sent from the retrofit box to the flat panel detector, a so-called exposure request signal. Hereupon a reset of the digital detector takes place. After expiration of this reset signal (in the order of magnitude of 100 microseconds) the digital detector is ready to detect the radiographic signal. Hereupon a signal is sent to the generator indicating the radiographic exposure can effectively start. Meanwhile the digital detector remains in the 'open' mode to capture the radiographic illumination. Since the generator delay time has effectively expired, the exposure starts, and the capture, resp. storage of the radiographic illumination signal by the digital detector takes place. A typical illumination time and corresponding integration time of the digital detector amounts to approx. 550 milliseconds.

In practical circumstances, use is often made of a three-point exposure, whereby an AEC (Automatic Exposure Control) module is used.

This is a method for controlling the radiographic illumination dose, known to the person skilled in the art.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:
1. A method for determining a delay time of a radiographic generator used in a medical radiographic system, and using the delay time as a standard operational value in the medical radiographic system, the method comprising the steps of:
(a) selecting a delay time for the radiographic generator on a retrofit box;
(b) simultaneously transmitting preparation and exposure signals from the retrofit box to a generator console; and
(c) determining whether, at an expiration of the selected delay time, a confirmation signal for a start of a radiographic exposure has been submitted by the radiographic generator; wherein in case a confirmation signal has been submitted, repeating the steps (a), (b), and (c) such that the delay-time is reduced by a factor of two;

in case no confirmation signal has been submitted, repeating once the steps (a), (b), and (c), and selecting a value for the delay time mid-way between a value when a confirmation signal has been obtained and a value when a confirmation signal has not been obtained anymore; and a last value of the selected delay time, in which a confirmation signal still has been provided by the radiographic generator, is retained as the standard operational value for the delay time of the medical radiographic system by the retrofit box.

2. The method according to claim 1, wherein an initial selected delay time is at least 10 seconds.

3. The method according to claim 1, wherein the preparation and exposure signals are transmitted simultaneously by simultaneous activation of preparation and exposure buttons on the retrofit box.

4. A method for taking a radiographic exposure in which a radiographic image is captured by a digital radiographic detector, the method comprising the steps of:
in case a radiographic operator generates an exposure signal to a retrofit box at a time that a delay time of a generator, counted from a submission of a preparation signal by the operator, has not yet expired, transmitting the exposure signal from the retrofit box to the radiographic generator after the expiration of a standard operational delay time as determined by the method according to claim 1 as counted from a transmission of the preparation signal from the retrofit box to the radiographic generator.

5. The method according to claim 4, wherein the retrofit box transmits the exposure signal to the radiographic generator after a positive reset signal has been received from the digital radiographic detector.

6. A radiographic recording system comprising:
a radiographic generator;
a generator console and an exposure unit;
a digital radiographic detector; and
a retrofit box including a detector to detect a preparation signal and an exposure signal, the retrofit box being configured to use a standard operational value as a delay time for transmission of the exposure signal to the radiographic generator; wherein
the radiographic recording system is configured to determine the standard operational value by:
(a) selecting a delay time for the digital radiographic generator on the retrofit box;
(b) simultaneously transmitting the preparation and exposure signals from the retrofit box to the generator console;
(c) determining whether, at an expiration of a selected delay time, a confirmation signal for a start of a radiographic exposure has been submitted by the radiographic generator;
in case a confirmation signal has been submitted, repeating the steps (a), (b), and (c) such that the delay time is reduced by a factor of two;
in case no confirmation signal has been submitted, repeating once the steps of (a), (b), and (c), and selecting a value for the delay time mid-way between a value when a confirmation signal has been obtained and a value when a confirmation signal has not been obtained anymore; and
a last value of the selected delay time, in which a confirmation signal still has been provided by the radiographic generator, is retained as a standard operational value for the delay time of the radiographic system by the retrofit box.

7. The radiographic recording system according to claim 6, wherein the detector includes a two-stage push button operationally coupled to the retrofit box.

* * * * *